(12) United States Patent
Verhaegh

(10) Patent No.: US 12,383,316 B2
(45) Date of Patent: Aug. 12, 2025

(54) LOCKING ASSEMBLY

(71) Applicant: Osseointegration International B.V., Ruurlo (NL)

(72) Inventor: Franciscus Theodorus Peter Verhaegh, Doesburg (NL)

(73) Assignee: Osseointegration International B.V., Ruurlo (NL)

( * ) Notice: Subject to any disclaimer, the term of this patent is extended or adjusted under 35 U.S.C. 154(b) by 185 days.

(21) Appl. No.: 18/002,280

(22) PCT Filed: Jul. 1, 2021

(86) PCT No.: PCT/NL2021/050412
§ 371 (c)(1),
(2) Date: Dec. 19, 2022

(87) PCT Pub. No.: WO2022/005283
PCT Pub. Date: Jan. 6, 2022

(65) Prior Publication Data
US 2023/0349409 A1  Nov. 2, 2023

(30) Foreign Application Priority Data

Jul. 3, 2020  (NL) .................................. 2025982

(51) Int. Cl.
*A61B 17/72* (2006.01)
*F16B 7/14* (2006.01)
(Continued)

(52) U.S. Cl.
CPC ...... *A61B 17/7225* (2013.01); *A61B 17/7291* (2013.01); *F16B 7/14* (2013.01);
(Continued)

(58) Field of Classification Search
CPC ............ A61B 17/7225; A61B 17/7241; A61B 17/7216; A61B 17/7233
See application file for complete search history.

(56) References Cited

U.S. PATENT DOCUMENTS 3,760,802 A * 9/1973 Fischer .............. A61B 17/7266
411/50
2010/0183399 A1  7/2010 Suga
(Continued)

FOREIGN PATENT DOCUMENTS

| CH | 619132 A5 * | 9/1980 |
| EP | 1544878 B1 | 8/2012 |
| GB | 2356907 A | 6/2001 |

OTHER PUBLICATIONS

English-language translation of CH 619132; accessed on Sep. 9, 2024 from EPO (Year: 2024).*

*Primary Examiner* — Julianna N Harvey
(74) *Attorney, Agent, or Firm* — B.V. Nederlandsch Octrooibureau

(57) ABSTRACT

An assembly for locking a mutual position between a secondary body (3) positioned inside a primary body (2), comprising an adjustment assembly (10) connectable to the primary body (2) and the secondary body (3) for mutual adjustment thereof along a longitudinal axis (A). The adjustment assembly (10) comprises an adjustment head (11) comprising an adjustment interface surface (13) for adjusting the mutual position, and a locking element (14) comprising a locking interface surface (13a). The locking element (14) is positioned coaxially to the adjustment head (11), wherein the adjustment head (11) and locking assembly (14) are mutually moveable along the longitudinal axis (A).

10 Claims, 3 Drawing Sheets

(51) Int. Cl.
  *F16B 7/18* (2006.01)
  *A61B 17/68* (2006.01)
  *A61B 17/86* (2006.01)

(52) U.S. Cl.
  CPC ........ *F16B 7/182* (2013.01); *A61B 2017/681* (2013.01); *A61B 17/725* (2013.01); *A61B 17/8605* (2013.01)

(56) References Cited

U.S. PATENT DOCUMENTS

2011/0054473 A1   3/2011  Brigido
2011/0282346 A1*  11/2011 Pham ................. A61B 17/1725
                                                606/62

* cited by examiner

LOCKING ASSEMBLY

FIELD OF THE INVENTION

The present invention relates to an assembly for locking a mutual position between a secondary body positioned inside a primary body, and, in a further aspect, a method for locking a mutual position between a secondary body positioned inside a primary body.

BACKGROUND ART

Such an assembly for locking a mutual position between two bodies being is well known in the state-of-the-art, and may require fixation of the two bodies using various fixation options, including screws, nuts, thread engagements, pin-slot and click-tab mechanisms.

SUMMARY OF THE INVENTION

The present invention seeks to provide an assembly based on a secondary body positioned inside a primary body, and locking the mutual thereof.

According to the present invention, an assembly for locking a mutual position between a secondary body positioned inside a primary body, comprising an adjustment assembly connectable to the primary body and the secondary body for mutual adjustment thereof along a longitudinal axis, the adjustment assembly comprising an adjustment head comprising an adjustment interface surface for adjusting the mutual position, and a locking element comprising a locking interface surface, the locking element being positioned coaxially to the adjustment head, wherein the adjustment head and locking element are mutually moveable along the longitudinal axis.

The present invention embodiments have the advantages that if offers an assembly having a small and compact structure, allowing for the use in applications with limited space, yet provide proper and secure locking of the mutual position between a primary and secondary body.

In a further aspect, the present invention relates to a method for locking a mutual position between a secondary body positioned inside a primary body, according to any one of the embodiments described herein.

SHORT DESCRIPTION OF DRAWINGS

Figure 1:
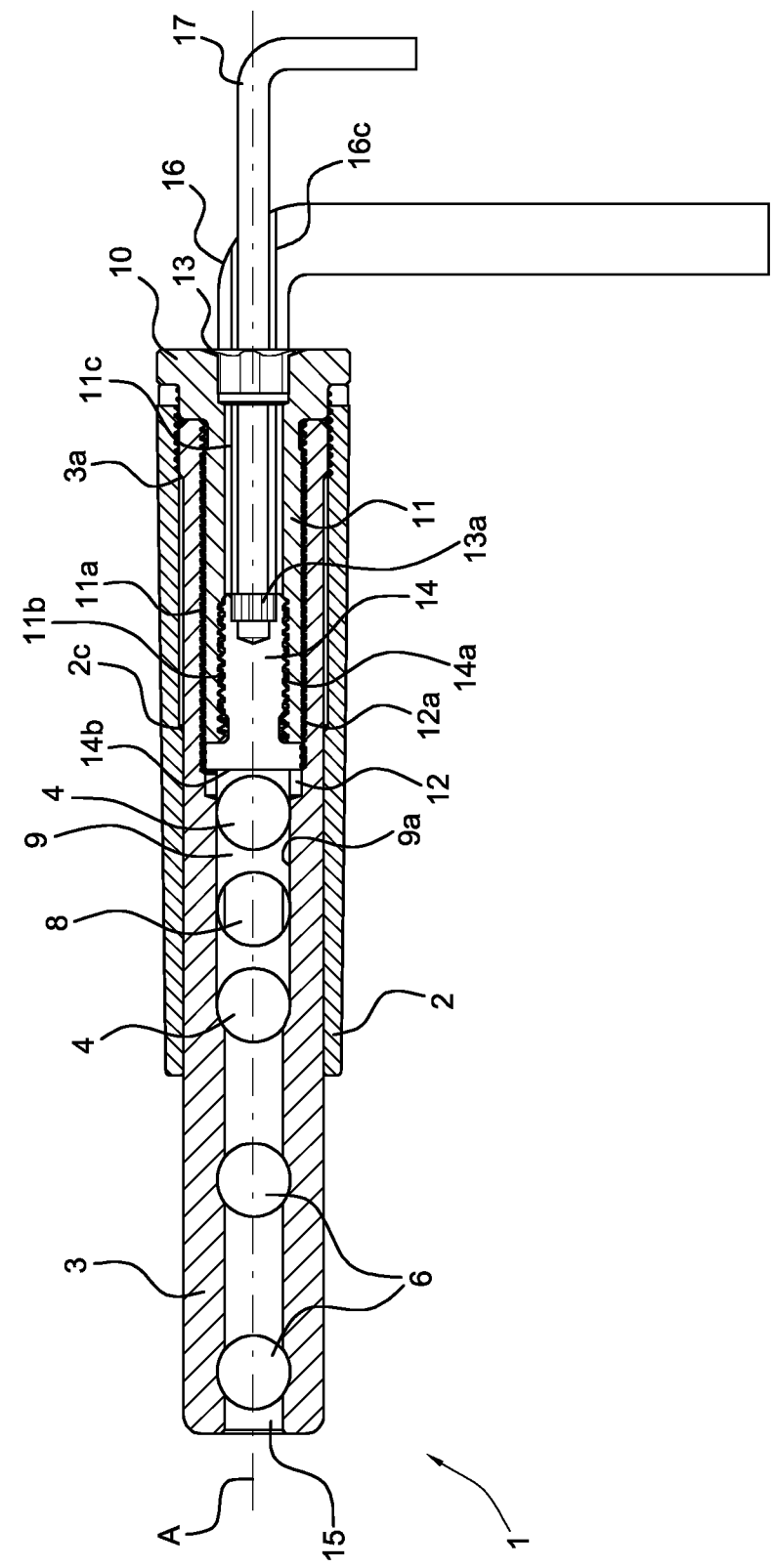
Figure 2:
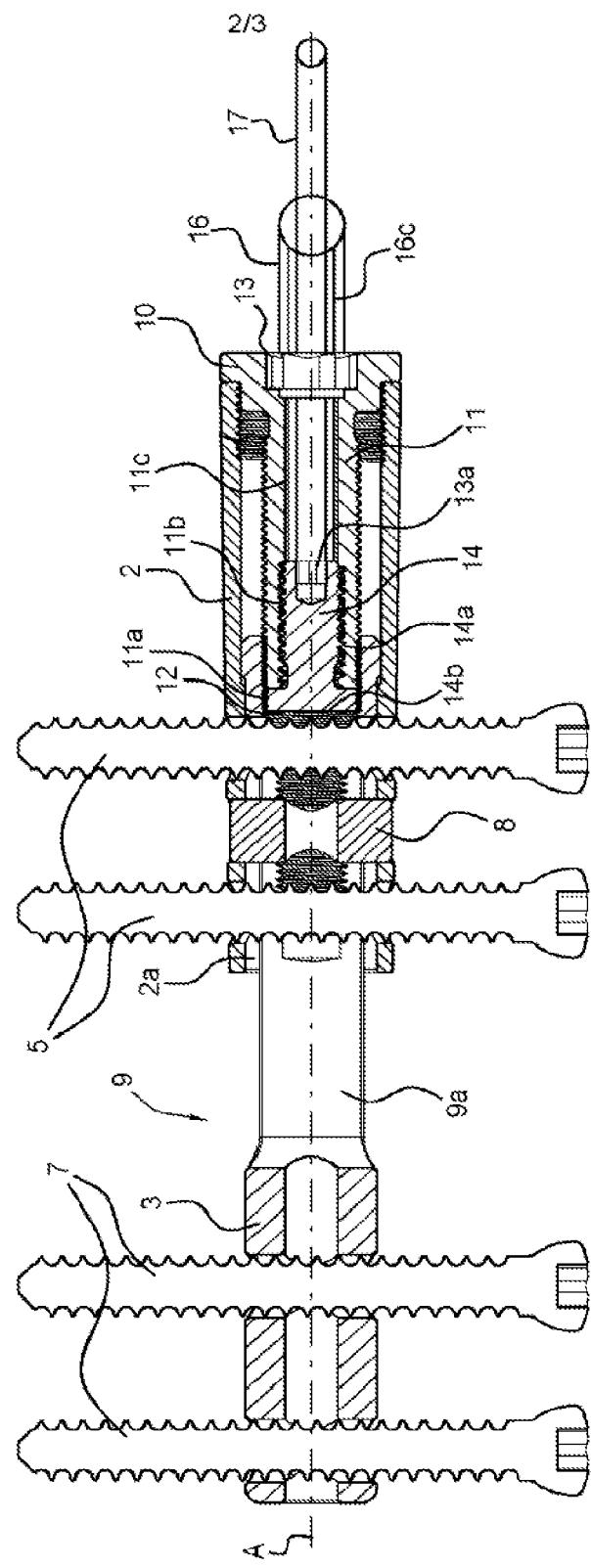
Figure 3:
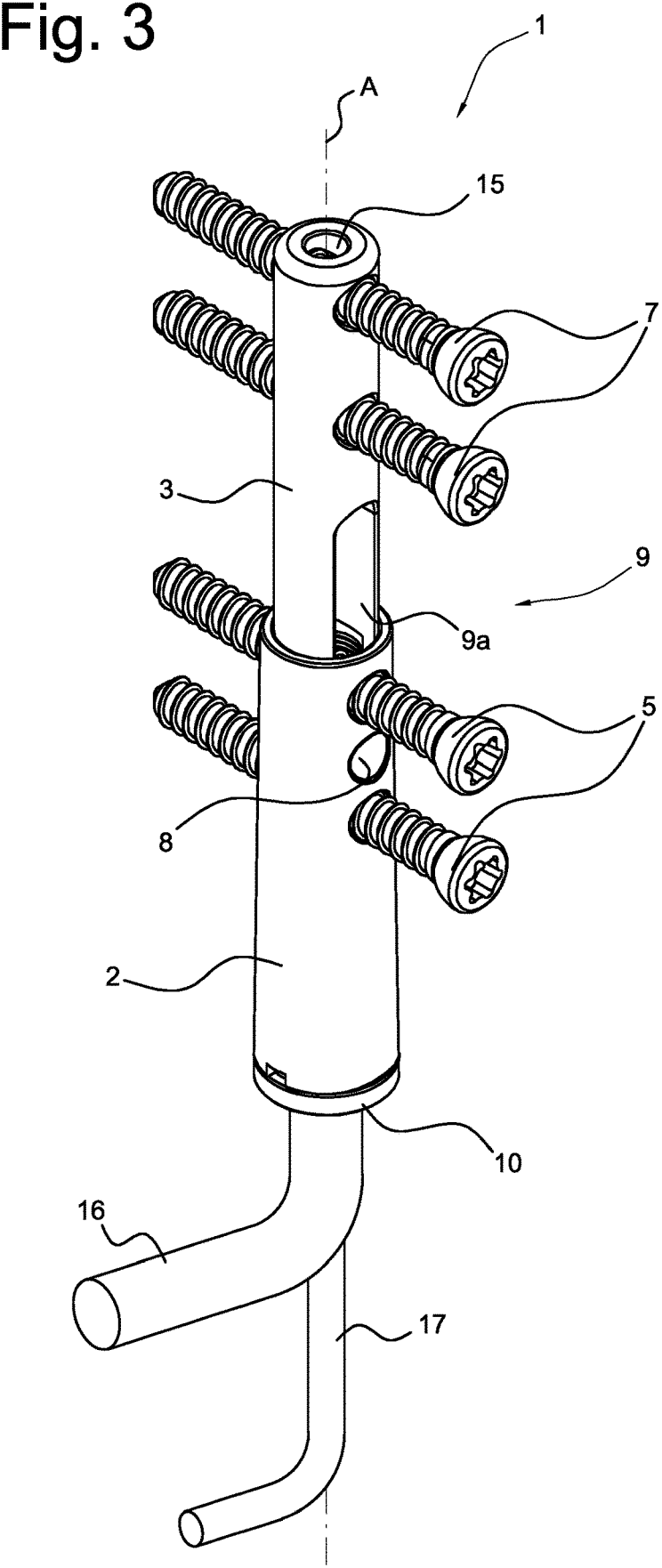

The present invention will be discussed in more detail below, with reference to the attached drawings, in which FIG. 1 shows a cross-sectional view of an assembly for locking a mutual position between a secondary body positioned inside a primary body, according to an embodiment of the present invention;

FIG. 2 shows a perpendicular cross-sectional view of the assembly of FIG. 1, and FIG. 3 shows a perspective view of the assembly embodiment of FIG. 2.

DESCRIPTION OF EMBODIMENTS

For many applications, a separate locking mechanism is needed for locking the mutual position of e.g. two rods positioned inside one another. Depending on the application, the space for locking the mutual position may be limited, and such a locking mechanism with a large structure and bulky components may not be suitable therefor. From this perspective, it would be desirable to provide a locking mechanism for small and compact spaces, yet, still allow good and secure locking of the mutual position.

The present invention embodiments provide an assembly having a smaller structure that is suitable for use in applications with limited spaces, yet, provide a simple and robust solution for locking the mutual position of e.g. two rods positioned inside one another with proper securement thereof.

FIG. 1 shows a cross-sectional view of an assembly for locking a mutual position between a secondary body 3 positioned inside a primary body 2, according to an embodiment of the present invention.

In the embodiment shown in FIG. 1, the assembly comprises an adjustment assembly 10 connectable to the primary body 2 and the secondary body 3 for mutual adjustment thereof along a longitudinal axis A. The secondary body 3 may be positioned in an inner bore 2a of the primary body 2 (see FIG. 2), and movable with respect to the primary body 2 by, for example, a thread engagement between an outer and inner screw thread. The adjustment assembly 10 is arranged to set and maintain the mutual position between the primary body 2 and secondary body 3.

In the embodiment shown in FIG. 1, the adjustment assembly 10 comprises an adjustment head 11 comprising an adjustment interface surface 13 for adjusting the mutual position, and a locking element 14 comprising a locking interface surface 13a, the locking element 14 being positioned coaxially to the adjustment head 11. As shown in FIG. 1, at least a part of the adjustment head 11 is positioned inside an adjustment bore 12 of the secondary body 3. The adjustment head 11 is configured to engage with the secondary body 3, and to adjust the mutual position of the primary body 2 and secondary body 3 via the adjustment interface surface 13. In an embodiment, the adjustment interface surface 13 may comprise a common screw drive arrangement, for example, a slotted or Phillips screw drive, that may allow a user to easily apply a rotational force to adjust the mutual position of the primary body 2 and secondary body 3 by e.g. a thread engagement. The adjustment interface surface 13 is provided at an end of the adjustment head 11 (see FIG. 1) for easy accessibility from the exterior environment.

Further, as shown in the embodiment in FIG. 1, the locking element 14 may also be positioned inside the adjustment bore 12 of the secondary body 3, and is moveable within the adjustment bore 12 along the longitudinal axis A, wherein the locking In this embodiment (as shown in FIG. 1), the adjustment head 11 and locking element 14 are mutually moveable along the longitudinal axis A. By engaging the locking interface surface 13a, the locking element 14 may move with respect to the adjustment head 11 using e.g. screw threads.

Once the mutual position has been adjusted by the adjustment interface surface 13, the locking element 14 may engage with the secondary body 3 to lock the position thereof, and, subsequently, also lock the mutual position of the primary body 2 and secondary body 3.

That is, the adjustment head 11 is arranged to adjust the mutual position, and, by moving the locking element 14 with respect to the adjustment head 11 to lock the (adjusted) mutual position, this may provide proper locking thereof in a secure, yet simple manner.

In more general wording, the present invention embodiments as described above all relate to an assembly for locking a mutual position between a secondary body 3 positioned inside a primary body 2, comprising an adjustment assembly 10 connectable to the primary body 2 and the secondary body 3 for mutual adjustment thereof along a longitudinal axis A, the adjustment assembly 10 comprising an adjustment head 11 comprising an adjustment interface surface 13 for adjusting the mutual position, and a locking element 14 comprising a locking interface surface 13a, the locking element 14 being positioned coaxially to the adjustment head 11, wherein the adjustment head 11 and locking element 14 are mutually moveable along the longitudinal axis A. This may provide an improved assembly having a small and compact structure for proper locking of a mutual position in a simple and robust manner.

To detail the advantageous characteristics of the assembly in relation to the present invention embodiments described here, the following non-limiting example is presented. The assembly is provided, wherein the adjustment assembly 10 is connected to the primary body 2 and the secondary body 3. The mutual position of the primary body 2 and secondary body 3 may (first) be adjusted by the adjustment interface surface 13 of the adjustment head 11, wherein the adjustment head 11 may engage with the secondary body 3 for co-operation thereof. Once the mutual position has been adjusted, the locking element 14 may engage with the adjustment head 11 for mutual movement thereof to lock the mutual position of the primary body 2 and secondary body 3.

From this perspective, since the adjustment assembly 10 is connected (and provided within) the primary body 2 and secondary body 3, by merely moving the locking element 14 with respect to the adjustment head 11, a simple solution is provided to lock the mutual position of the primary body 2 and secondary body 3, using an assembly with a small and compact structure.

In an embodiment shown in FIG. 1, the assembly further comprises an adjustment key 16 co-operating with the adjustment interface surface 13, and a fixation key 17 co-operating with the locking interface surface 13a. As shown in FIG. 1, an end of the adjustment key 16 may engage with the adjustment interface surface 13 for co-operation thereof, and an end of the fixation key 17 may engage with the locking interface surface 13a for co-operation thereof. As an exemplary example, the adjustment key 16 may be rotated to co-operate with the adjustment interface surface 13 to engage a screw thread arrangement thereof.

The adjustment key 16 and fixation key 17 are both generally and similarly L-shaped (for e.g. easy rotation thereof) to allow a user to engage the adjustment interface surface 13 and locking interface surface 13a, respectively, in a more effective and direct manner.

In a further embodiment shown in FIG. 1, the fixation key 17 is positioned inside an inner bore 11c of the adjustment head 11 and an inner bore 16c of the adjustment key 16. A width of the fixation key 17 may be smaller than a width of both the inner bore 11c of the adjustment head 11 and inner bore 16c of the adjustment key 16 for easy positioning of the fixation key 17 therein. As shown in FIG. 1, the inner bore 11c of the adjustment head 11 may be positioned co-axially with the inner bore 16c of the adjustment key 16 to allow the fixation key 17 to be positioned and inserted in a straight and parallel manner, allowing the fixation key 17 is able to move with respect to the adjustment key 16 in a sliding manner.

In view of this, one opening of the inner bore 11c of the adjustment head 11 may be provided on the adjustment interface surface 13, and another opening provided on the locking interface surface 13a, wherein the openings are positioned co-axially with one another (shown in FIG. 1).

By presence of the inner bore 11c of the adjustment head 11, easy accessibility of the locking interface surface 13a for the fixation key 17 is provided.

To elaborate further on this embodiment, a further non-limiting example is provided. An end of the adjustment key 16 may engage the adjustment interface surface 13, and the fixation key 17 may be inserted into the inner bore 16c of the adjustment key 16, and through the inner bore 11c of the adjustment head 11 to engage with the locking interface surface 13a. By keeping the fixation key 17 stationary in position to avoid any mutual movement, the adjustment key 16 may co-operate with the adjustment interface surface 13 (e.g. by rotational movement) to adjust the mutual position between the primary body 2 and secondary body 3. Thereafter, by keeping the adjustment key 16 stationary in position, the fixation key 17 may co-operate with the locking interface surface 13a to engage the locking element 14 and lock the mutual position. Both the adjustment key 16 and fixation key 17 may subsequently be removed, leaving the mutual position in a proper locked status. If desired, the mutual position may be unlocked using a similar approach, i.e. re-engaging the adjustment interface surface 13 and locking interface surface 13a.

In this respect, the inner bores 11c, 16c for insertion of the fixation key 17 therein provides an even more efficient and compact assembly with minimal dimensions, yet allow effective and direct locking of the mutual position.

To that end, in an even further embodiment, the locking interface surface 13a comprises a common screw drive arrangement, e.g. an Allen screw drive, or a Phillips screw drive, allowing a user to easily apply a rotational force to engage e.g. a thread engagement and allow mutual movement of the locking element 14 and the adjustment head 11 along the longitudinal axis A. Many exemplary examples of a common screw drive arrangement are known to the skilled person, including Robertson, hex and (security) torx screw drives.

In yet a further embodiment shown in FIG. 1, the locking element 14 comprises an abutting surface 14b. The abutting surface 14b may be positioned co-axially (and opposite) to the locking interface surface 13a. As already mentioned herein, the locking element 14 and adjustment head 11 are mutually moveable along the longitudinal axis A. With this in mind, owing to the movement of the locking element 14, the abutting surface 14b is arranged to move and abut (i.e. is forced) against e.g. a surface of the secondary body 3 for an abutting engagement thereof, and subsequently lock the mutual position.

As known to the skilled person, by having an abutting engagement with the abutting surface 14b, due to the high tension forces, this may prevent any (unintentional) axial movement of the locking element 14 (relative to the adjustment head 11) along the longitudinal axis A to provide strong locking of the mutual position.

The abutting surface 14b may comprise a flat surface, but other implementations and exemplary components, including flanges or ridges, may be envisaged and known to the skilled person.

In the exemplary embodiment shown in FIG. 1, the adjustment head 11 has a first screw thread 11a, wherein the first screw thread 11a is configured to engage with a second screw thread 12a of the adjustment bore 12 of the secondary body 3. The first screw thread 11a may comprise an outer screw thread on an outer circumferential surface of the adjustment head 11, and the second screw thread 12a may comprise an inner screw thread on an inner circumferential surface of the adjustment bore 12. If a sufficiently high external rotational force is present to engage the thread engagement between the first screw thread 11a and the second screw thread 12a, the primary body 2 may move with respect to the secondary body 3, thereby adjusting the mutual position. An outside surface of the locking element 14 which is flush with the outside surface of the adjustment head 11 may be provided with a similar first screw thread 11a, allowing the combination of adjustment head 11 and locking element 14 to move within the adjustment bore 12 (second screw thread 12a) when rotated synchronously, and to lock the assembly 10 when rotated independently using adjustment interface surface 13 and locking interface surface 13a. In further embodiments, the abutting surface 14b as described above may be provided as an alternative for the similar first screw thread 11a on the outside surface of the locking element 14 as locking mechanism co-operating with the secondary body 3.

In a further exemplary embodiment shown in FIG. 1, the locking element 14 has a third screw thread 14a co-operating with a fourth screw thread 11b of the adjustment head 11. Similar to embodiment described herein for the first screw thread 11a, by applying an external rotational force on the locking interface surface 13a on the locking element 14, this may engage a thread engagement between the third screw thread 14a and the fourth screw thread 11b, thereby allowing the locking element 14 to move with respect to the adjustment head 11. In this configuration, due to tension forces acting on the third and fourth screw threads 14a, 11b, any unintentional mutual movement of the adjustment head 11 and locking element 14 along the longitudinal axis A is prevented for stronger locking of the mutual position.

In an even further exemplary embodiment shown in FIG. 1, the third screw thread 14a comprises an outer screw thread and the fourth screw thread 11b comprises an inner screw thread. The third screw thread 14a is provided on an outer circumferential surface of the locking element 14, and the fourth screw thread 11b is provided on an inner circumferential surface of the adjustment bore 12, as shown in FIG. 1.

In an advantageous embodiment shown in FIG. 1, a screw thread pitch of the third screw thread 14a and fourth screw thread 11b is unequal to a screw thread pitch of the first screw thread 11a. As known to the skilled person, in general, an unequal screw thread pitch, e.g. a smaller screw thread pitch, is, both in tension and shearer forces, stronger than a larger screw thread pitch, and also has a lesser tendency to loosen. From this standpoint, by having a smaller screw thread pitch in the third screw thread 14a/fourth screw thread 11b combination than in the first screw thread 11a, a very efficient and robust locking mechanism is provided.

In a specific embodiment, a length of the third screw thread 14a and/or fourth screw thread 11b is at least 1 mm, e.g. 5 mm, allowing for a sufficient number of screw threads for mutual movement of the adjustment head 11 and locking element 14. In a further advantageous embodiment, a length of the locking element 14 along the longitudinal direction A is smaller than a length of the adjustment head 11 along the longitudinal direction A. This does not only provide for a very compact structure, but, as shown in FIG. 1, the locking element 14 may nicely fit into the adjustment head 11 and conceal any of the unequal and hidden operation interfaces (e.g. locking interface surface 13a) within the adjustment head 11.

In a further aspect relating to the embodiments described herein, as shown in FIG. 1, the present invention also relates to a device 1 for bone compression with a longitudinal axis A comprising a secondary body 3 positioned inside a primary body 2, and the assembly according to any one of the embodiments described herein. In the exemplary, non-limiting application, the device 1 may be suitable for bone compression of small bones in the foot or ankle. In general, good, sustained compression between bone parts is highly desirable, and the space in the foot and ankle is rather limited due to the presence of small bones and the structure thereof. In this context, by fixing the primary body 2 and secondary body 3 to respective bone parts and applying compression between the bone parts, the assembly may be used to lock the mutual position of the primary body 2 and secondary body 3, thereby maintaining the sustained compression in a simple yet proper manner. Moreover, the small and compact structure of the assembly (and device 1) is suitable for the limited space in the foot or ankle.

As shown in FIG. 1, in this further aspect, the primary body 2 may extend along the longitudinal axis A, wherein the primary body 2 has an inner bore 2a with a primary internal diameter (see FIG. 2), and a fixation pins 5 extending at an angle to the longitudinal axis A.

The secondary body 3 may also extend along the longitudinal axis A, wherein the secondary body 3 has an outer diameter smaller than the primary internal diameter, and fixation pins assembly 7 extending at an angle to the longitudinal axis A.

The primary body 2 comprises a guide pin 8 positioned perpendicular to the longitudinal axis A, and the secondary body 3 comprises a guide slot 9, the guide pin 8 extending through the guide slot 9. The guide slot 9 may also have an inner guide surface 9a.

In a further embodiment (shown in FIG. 1) relating to the device 1, the secondary body 3 and the primary body 2 are provided with respective abutment surfaces 3a, 2c, arranged to limit the movement of the secondary body 3 with respect to the primary body 2.

In certain embodiments relating to the device 1, as shown in FIGS. 1 and 2, the fixation pins 4 extend through two apertures 4 in the primary body 2 positioned on two opposite sides of the guide pin 8. Similarly, in other embodiments relating to the device 1 and also shown in FIGS. 1 and 2, the fixation pins 7 extend through two apertures 6 in the secondary body 3.

In an even further embodiment in relation to this further aspect, device 1 may comprise a cannulation channel 15 along the longitudinal direction A for e.g. passing a guide wire there through. The channel width of the cannulation channel 15 is e.g. more than 3.2 mm.

It is noted that FIG. 2 shows a cross-sectional view of the device 1 in FIG. 1, including the fixation pins 5, 7, and FIG. 3 shows a perspective view of the device 1 in FIG. 2.

In yet an even further aspect, the present invention relates to a method for locking a mutual position between a secondary body 3 positioned inside a primary body 2, comprising connecting an adjustment assembly 10 to the primary body 2 and the secondary body 3 for mutual adjustment thereof along a longitudinal axis A, wherein the adjustment assembly 10 comprises an adjustment interface surface 13 for adjusting the mutual position, and a locking element 14 comprising a locking interface surface 13a, the locking element 14 being positioned coaxially to the adjustment head 11, and engaging the locking element 14 with the adjustment head 11 for mutual movement thereof along the longitudinal axis A.

As already mentioned herein, the adjustment head 11 may be positioned inside an adjustment bore 12 of the secondary body 3. Furthermore, in an exemplary method embodiment, the engagement of the locking element 14 with the adjustment head 11 may comprise a thread engagement with respective inner and outer screw threads to provide a mutual movement thereof by rotating the locking interface surface 13a.

In a further embodiment, the method further comprises engaging an adjustment key 16 with the adjustment interface surface 13 for co-operation thereof, and engaging a fixation key 17 with the locking interface surface 13a for co-operation thereof. An end of the adjustment key 16 may engage with the adjustment interface surface 13, and an end of the fixation key 17 may engage with the locking interface surface 13a.

In an even further embodiment, the method further comprises positioning the fixation key 17 inside an inner bore 11c of the adjustment head 11 and an inner bore 16c of the adjustment key 16. The adjustment key 16 may first engage the adjustment interface surface 13 such that the inner bore 16c of the adjustment key 16 is positioned co-axially to the inner bore 11c of the adjustment head 11, where, thereafter, the fixation key 17 may be inserted into the inner bore 16c of the adjustment key 16, and through the inner bore 11c of the adjustment head 11 to engage with the locking interface surface 13a.

Alternatively, the fixation key 17 may first be inserted into the inner bore 16c of the adjustment key 16, where, thereafter, the adjustment key 16 may engage the adjustment interface surface 13, and the fixation key 17 is then inserted through the inner bore 11c of the adjustment head 11 to engage with the locking interface surface 13a.

The present invention has been described above with reference to a number of exemplary embodiments as shown in the drawings. Modifications and alternative implementations of some parts or elements are possible, and are included in the scope of protection as defined in the appended claims.

The invention claimed is:

1. An assembly for locking a mutual position between a secondary body positioned inside a primary body, comprising:
   an adjustment assembly connectable to the primary body and the secondary body for mutual adjustment thereof along a longitudinal axis, the adjustment assembly comprising,
   an adjustment head comprising an adjustment interface surface for adjusting the mutual position, and a locking element comprising a locking interface surface, the locking element being positioned coaxially to the adjustment head, and wherein the locking element is longitudinally movable relative to the adjustment head by engaging the locking interface surface for locking the mutual position between the primary body and the secondary body,
   wherein the adjustment head and the locking element each comprise an outer screw thread configured for engagement with an inner screw thread of an adjustment bore of the secondary body, and
   wherein the adjustment head and locking element are mutually moveable along the longitudinal axis through the adjustment bore when rotated synchronously with respect to the secondary body, further comprising,
   an adjustment key co-operating with the adjustment interface surface, and a fixation key co-operating with the locking interface surface.

2. The assembly according to claim 1, wherein the fixation key is positioned inside an inner bore of the adjustment head and an inner bore of the adjustment key.

3. The assembly according to claim 1, wherein the locking element has a further outer screw thread co-operating with an inner screw thread of the adjustment head.

4. The assembly according to claim 3, wherein a screw thread pitch of the further outer screw thread of the locking element and inner screw thread of the adjustment head is unequal to a screw thread pitch of the outer screw thread of the adjustment head.

5. The assembly according to claim 3, wherein a length of the third further outer screw thread of the locking element and/or inner screw thread of the adjustment head is at least 1 mm.

6. The assembly according to claim 1, wherein the locking interface surface comprises a common screw drive arrangement.

7. The assembly according to claim 1, wherein a length of the locking element along the longitudinal axis is smaller than a length of the adjustment head along the longitudinal axis.

8. A device for bone compression with a longitudinal axis comprising a secondary body positioned inside a primary body, and the assembly according to claim 1.

9. A method for locking a mutual position between a secondary body positioned inside a primary body, comprising:
   connecting an adjustment assembly to the primary body and the secondary body for mutual adjustment thereof along a longitudinal axis,
   wherein the adjustment assembly comprises an adjustment head comprising an adjustment interface surface for adjusting the mutual position, and a locking element comprising a locking interface surface, the locking element being positioned coaxially to the adjustment head, and wherein the locking element is longitudinally movable relative to the adjustment head by engaging the locking interface surface, and
   engaging an adjustment key with the adjustment interface surface for co-operation thereof, and engaging a fixation key with the locking interface surface for co-operation thereof,
   engaging the locking element with the adjustment head for mutual movement thereof along the longitudinal axis, further comprising
   engaging the adjustment key for movement of the secondary body relative to the primary body; and
   engaging the fixation key for longitudinal movement of the locking element relative to the adjustment head.

10. The method according to claim 9, further comprising positioning the fixation key inside an inner bore of the adjustment head and an inner bore of the adjustment key.

* * * * *